United States Patent [19]

Moutafis et al.

[11] Patent Number: 5,713,878
[45] Date of Patent: Feb. 3, 1998

[54] HAND TIGHTENABLE HIGH PRESSURE CONNECTOR

[75] Inventors: Timothy E. Moutafis, Gloucester; C. Ronald Coffin, Topsfield, both of Mass.

[73] Assignee: Surgi-Jet Corporation, Wilmington, Mass.

[21] Appl. No.: 473,406

[22] Filed: Jun. 7, 1995

[51] Int. Cl.$^6$ .................................................. A61M 25/00
[52] U.S. Cl. .................................................. 604/283
[58] Field of Search .................................. 604/240, 283, 604/905; 285/347–349, 331, 353

[56] References Cited

U.S. PATENT DOCUMENTS

| | | |
|---|---|---|
| 3,818,913 | 6/1974 | Wallach . |
| 3,930,505 | 1/1976 | Wallach . |
| 3,989,283 | 11/1976 | Pepper . |
| 4,111,490 | 9/1978 | Liesveld . |
| 4,465,438 | 8/1984 | Bräuer et al. . |
| 4,560,373 | 12/1985 | Sugino . |
| 4,690,672 | 9/1987 | Veltrup . |
| 4,761,039 | 8/1988 | Hilaris . |
| 4,776,616 | 10/1988 | Umehara et al. . |
| 4,776,769 | 10/1988 | Hilaris . |
| 4,795,217 | 1/1989 | Hilaris . |
| 4,798,339 | 1/1989 | Sugino et al. . |
| 4,811,902 | 3/1989 | Nagata . |
| 4,827,679 | 5/1989 | Earle, III . |
| 4,898,574 | 2/1990 | Uchiyama et al. . |
| 4,913,698 | 4/1990 | Ito et al. . |
| 4,932,114 | 6/1990 | Morse et al. . |
| 4,937,985 | 7/1990 | Boers . |
| 4,950,238 | 8/1990 | Sullivan . |
| 5,018,670 | 5/1991 | Chalmers . |
| 5,037,431 | 8/1991 | Summers . |
| 5,052,624 | 10/1991 | Boers . |
| 5,074,862 | 12/1991 | Rausis . |
| 5,092,744 | 3/1992 | Boers . |
| 5,125,582 | 6/1992 | Suriaatmadja et al. . |
| 5,133,687 | 7/1992 | Malloy . |
| 5,135,482 | 8/1992 | Neracher . |
| 5,162,016 | 11/1992 | Malloy . |
| 5,171,045 | 12/1992 | Pasbrig . |
| 5,205,779 | 4/1993 | O'Brien et al. . |
| 5,314,375 | 5/1994 | O'Brien et al. . |
| 5,322,504 | 6/1994 | Doherty . |
| 5,370,609 | 12/1994 | Drasler . |
| 5,468,028 | 11/1995 | Olson . |
| 5,474,336 | 12/1995 | Hoff et al. . |
| 5,496,267 | 3/1996 | Drasler et al. . |
| 5,509,911 | 4/1996 | Cottone, Sr. et al. . |
| 5,511,830 | 4/1996 | Olson et al. . |

OTHER PUBLICATIONS

Tikhomiroy, R.A. et al, High–Pressure Jet Cutting TJ840 G5313 (1992).

*Primary Examiner*—Manuel Mendol
*Attorney, Agent, or Firm*—Wolf, Greenfield & Sacks P.C.

[57] ABSTRACT

A hand tightenable connector provides a high pressure seal between a first element and a second element. A first female element includes a recess for supporting a compressible O-ring and a second male element includes a ferrule which deforms the O-ring in the recess when the male and female elements are mated. The ferrule abuts against the surface defining the opening of the O-ring recess so that a high pressure seal is effected between the first and second elements without severely distorting the O-ring. The connector may be used to couple various components of a high pressure fluid delivery system such as are found in a jet cutting system.

22 Claims, 2 Drawing Sheets

5,713,878

HAND TIGHTENABLE HIGH PRESSURE CONNECTOR

FIELD OF INVENTION

The invention relates to a high pressure fluid seal and, more particularly, to a hand tightenable connector for sealing components of a high pressure fluid jet system.

BACKGROUND OF THE INVENTION

Elastomeric O-rings are commonly employed to seal surfaces where the pressure is not expected to exceed 700 p.s.i. At greater pressures, special materials and sealing configurations are typically required. Many high pressure seals rely on a combination of a metal-to-metal seal with an initial seal made by a gasket formed of soft material. Tightening of the metal-to-metal seal compresses the soft material severely, impairing the removal of the gasket which may be disadvantageous when one or more of the sealed components are intended to be frequently replaced.

SUMMARY OF THE INVENTION

The present invention is a hand tightenable connector for providing a high pressure seal between a first and second element. A first female element includes a recess for supporting a compressible O-ring and a second male element includes a ferrule which deforms the O-ring in the compatible gland when the male and female elements are mated. The ferrule abuts against the surface defining the opening to the O-ring recess, but does not reduce the volume of the annulus. The first element may include a chamber, contiguous with the O-ring recess, which is adapted to receive the ferrule. A hand tightenable connector may be threadably engaged with the first body, drawing the ferrule into seating engagement in the chamber. The ferrule bottoms out against the floor of the chamber, deforming the O-ring a predetermined amount, but no more, so that a high pressure seal is affected between the first and second element without severely distorting the gasket so that the O-ring can be easily removed when the first and second bodies are separated.

The present invention also includes a high pressure connection between a pressure resistant delivery tube of a fluid jet cutting system and either a jetting instrument or an outlet of a pump which generates the high pressure fluid. The coiled delivery tube includes a straight segment on one or both ends which is permanently fitted with a ferrule. An O-ring is slidably mounted over the tube end until it abuts the ferrule. The protruding tip of the delivery tube is received by an inlet of the jet wand or the outlet port of the pump. A thumb screw or other fastening mechanism draws the ferrule and O-ring into seating engagement in a stepped chamber having a reduced dimensioned recess for the O-ring and a larger chamber for the ferrule. The thumbscrew and ferrule may be configured to provide compatible surfaces, facilitating insertion of the ferrule into the stepped chamber as the thumbscrew and jet wand or outlet port are threadably engaged.

It is an object of the present invention to provide a high pressure seal employing an elastomeric O-ring.

It is another object of the present invention to provide a high pressure seal between components of a high pressure fluid jet cutting system.

It is another object of the invention to provide a hand-tightenable connection which is adapted to withstand high pressures and allow for a quick disconnect and connect of various components of the jet cutting system.

It is a still further object of the present invention to provide a detachable high pressure seal.

Other objects and features of the present invention will become apparent from the following detailed description when taken in connection with the accompanying drawings which disclose multiple embodiments of the invention. It is to be understood that the drawings are designed for the purpose of illustration only and are not intended as a definition of the limits of the invention.

DESCRIPTION OF THE DRAWINGS

The foregoing and other objects and advantages of the invention will be appreciated more fully from the following drawings in which.

DESCRIPTION OF THE INVENTION

Figure 1:
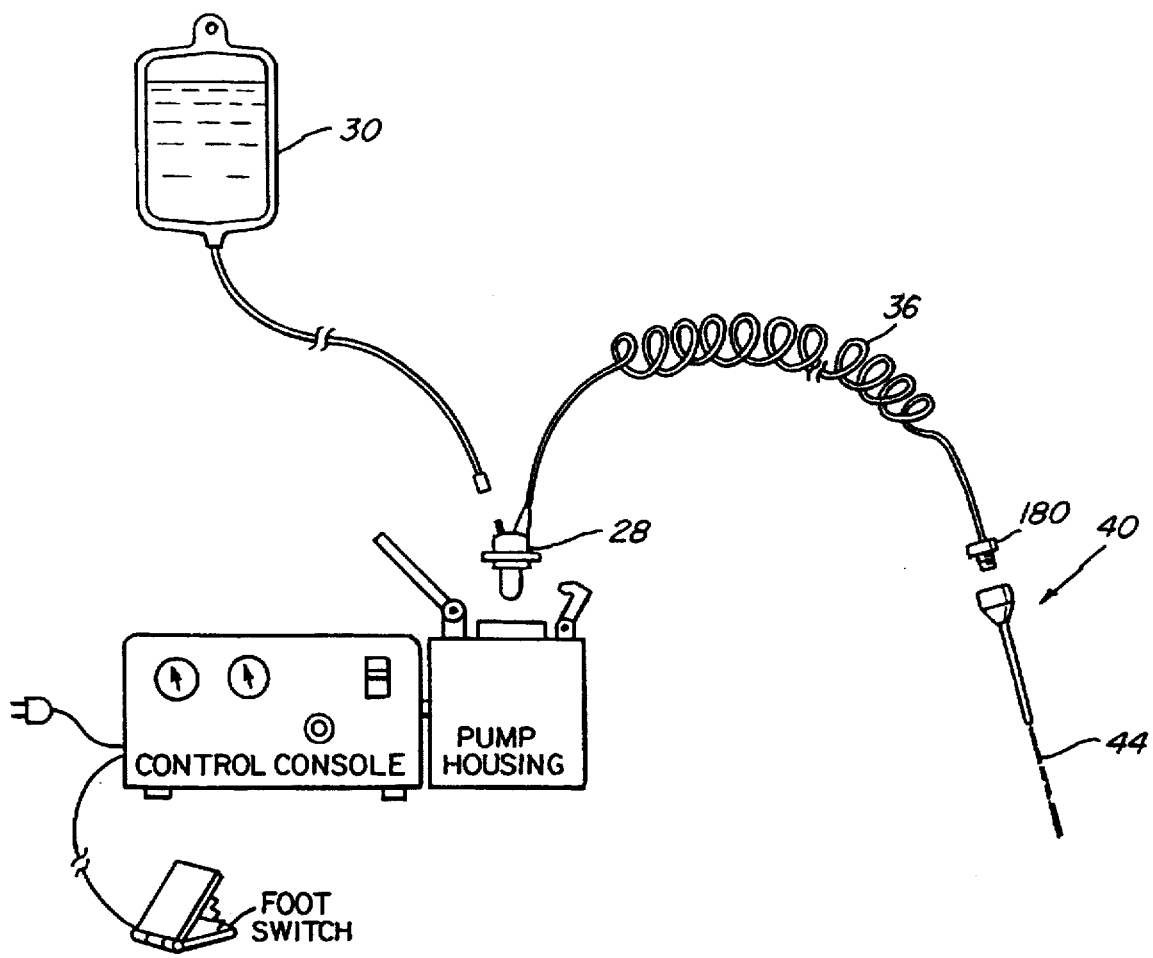
FIG. 1 is a schematic of a fluid jet cutting system.

The present invention is a hand tightenable high pressure seal or connector. Although described below in reference to a fluid jet cutting system, the quick connector may be employed in other applications. A representative fluid jet arrangement is illustrated in FIG. 1 and includes a source of solution 30 to be jetted, such as saline, a variable pressure pump 28 for forcing the saline at high pressure through a burst resistant delivery tube 36 and into a nozzle instrument 40 or wand having one or more orifices for creating the jet stream 44 as the saline exits therefrom. Alternatively, the jet instrument may embody a burst resistant catheter having a jet tip such as is disclosed in U.S. Pat. No. 5,370,609, the contents of which are incorporated herein by reference. The delivery tube may be coiled, enhancing the flexibility of the tube and the ease of handling by a user.

A high pressure seal is formed between the delivery tube and the pump outlet and between the jet creating instrument 40 and the delivery tube, ensuring leaktight operation even at pressures of 50,000 p.s.i. and beyond. The seal preferably is provided in a hand-tightenable and releasable connector where one or both of the foregoing junctions are detachable rather than permanent.

Figure 2:
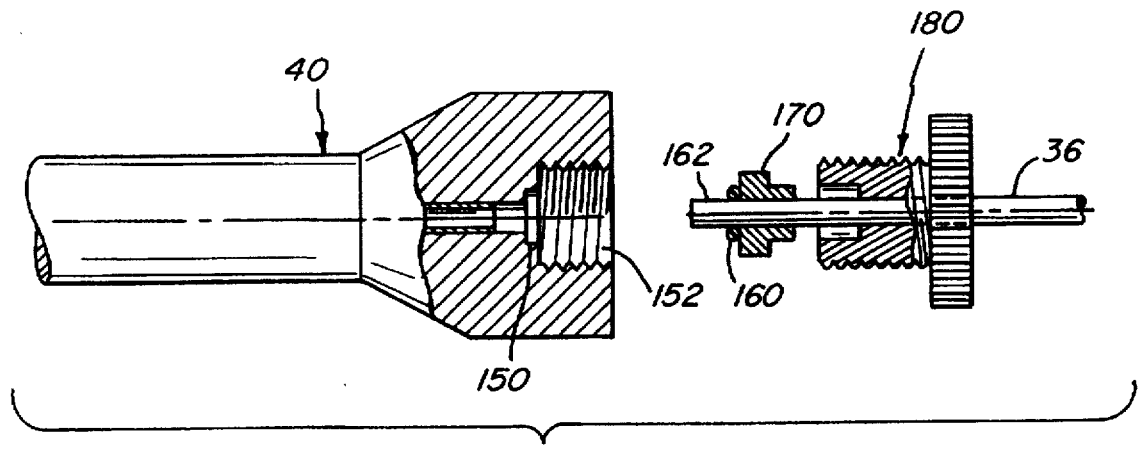
FIG. 2 is an illustration of the components used to provide a high pressure seal between a jet nozzle and a burst resistant delivery tube.
Figure 3:
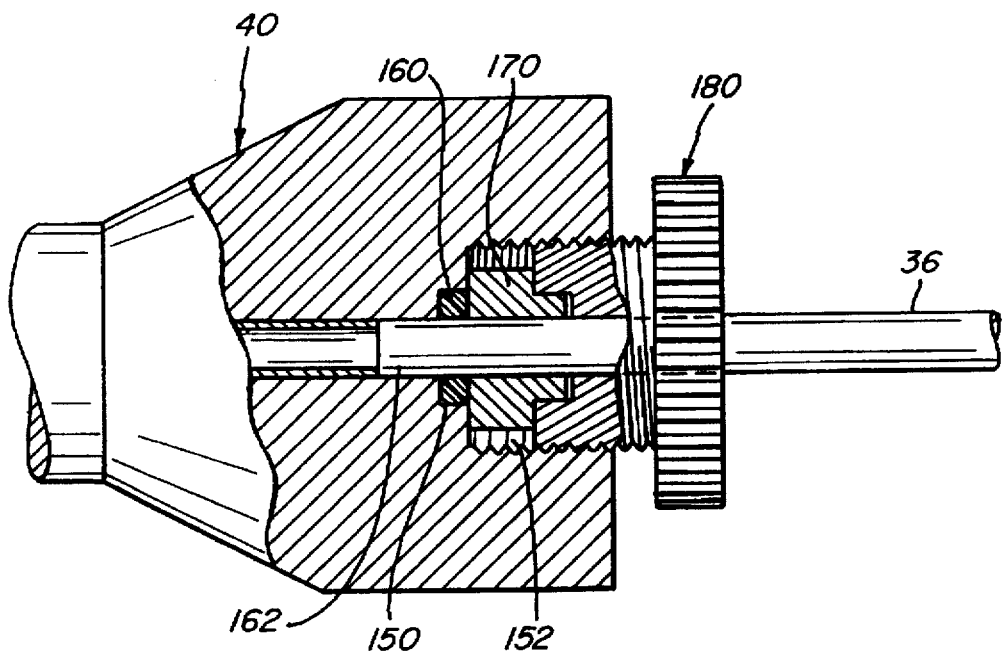
FIG. 3 is an illustration of the high pressure seal after connecting the components illustrated in FIG. 2.

The high pressure connector will be described in reference to the junction of the delivery tube and surgical instrument. A similar sealing arrangement may be employed in the connection of the pump outlet and the delivery tube. With reference to FIGS. 2 and 3, a proximal end of the jet instrument 40 is threadably engageable with the distal end of the delivery tube 36. A reduced diameter recess 150 in a stepped chamber 152 in the jet wand 40 is adapted to receive an elastomeric or other soft material O-ring 160 carried by an uncoiled distal segment 162 of the delivery tube. The O-ring is mounted against a ferrule 170 which is brazed, or otherwise permanently attached, to the delivery tube. A captive threaded connector 180 advances the ferrule, which reciprocally moves the O-ring, towards the stepped chamber as the jet instrument and delivery tube are tightened together. The ferrule bottoms out against the floor of the larger chamber so that the O-ring is deformed a predetermined amount within the smaller recess, but no further. The O-ring seals the connection of the delivery tube and jet handpiece, actually deforming to fill the entire recess, allowing fluidtight flow from the lumen of the delivery tube, through the jet wand lumen and out of the jet orifice.

In a representative embodiment, the O-ring is formed of medical grade Buna-N, such as the Apple-003 (ARP 568 Uniform No. Std.). The O-ring has nominal inner and outer diameters of 1/16th and 3/16th inches, respectively, and is 1/16th inches thick. The actual outer diameter is 0.056±0.006 inches and the actual thickness is 0.060±0.006 inches The O-ring recess has a diameter of 0.195 inches and a height of 0.045 inches. The ferrule receiving chamber has a diameter of about 0.38 inches and 18 threads per inch. When inserted, the inner diameter of the O-ring is bounded by the hypo tube which has an outer diameter of 0.058 inches. Consequently, the O-ring deforms when the ferrule abuts the floor of the stepped chamber. It is believed that the modulus of elasticity of the elastomeric O-ring approaches that of a hard plastic, or a soft metal, when deformed in the fashion described above. A high pressure connector according to the present invention has been used in a fluid jet cutting system at pressures up to 20,000 p.s.i. without leakage.

In addition to providing safe fluid conveyance, the hand tightenable connector permits a surgeon to easily switch amongst different instruments during a procedure. After halting the flow of the fluid jet, the surgeon simply unscrews the captive connector and removes the distal end of the delivery tube from the mouth of the jet instrument. A fresh, sterile instrument is then mated which has a new O-ring against the ferrule. After tightening the connector, the procedure may continue.

Although the male component of the sealing mechanism is illustrated on the delivery tube and the female component is shown on the jet instrument, the orientation may be reversed to accomplish the objective of the invention. Further, while a threaded connection is employed to join the connector and jet wand, other arrangements for releasably securing the components together could be employed as would be apparent to one of skill in the art, such as a quick connect, snap fastener.

It should be understood that the foregoing description of the invention is intended merely to be illustrative thereof and other equivalents, embodiment and modifications of the invention may be apparent to those artisans.

What is claimed is:

1. A high pressure seal, comprising:
   a first element having a lumen extending therethrough and a first recess, in communication with said lumen, with a defined volume;
   a deformable seal having a natural configuration which is similarly shaped but which has a thickness slightly larger than the height of said first recess, said seal being positioned in said first recess and having an opening therethrough;
   a second element having a portion thereof extending through said opening in said seal and into said lumen of said first element, said first and second elements being configured and arranged for relative movement therebetween; and
   a ferrule carried by a portion of said second element, and which is larger than said first recess, said ferrule contacting said seal upon relative movement of said first and second element to deform said seal such that said seal substantially fills the first recess, without reducing said defined volume of said first recess.

2. The high pressure seal recited in claim 1 wherein said second element includes a lumen which is in communication with said lumen of said first element.

3. The high pressure seal recited in claim 1 wherein said first element includes a second recess adapted to receive said ferrule, said second recess being larger than said first recess and in communication with said first element lumen.

4. The high pressure seal recited in claim 3 wherein said second recess is contiguous with said first recess.

5. The high pressure seal recited in claim 4 wherein said first and second recesses form a stepped chamber.

6. The high pressure seal recited in claim 1 wherein said seal is an elastomer.

7. The high pressure seal recited in claim 1 wherein said seal in an O-ring.

8. The high pressure seal recited in claim 1 further including a hand tightenable connection for securing said first and second elements together.

9. The high pressure seal recited in claim 8 wherein said hand tightenable connection includes a hand tightenable connector carried by said second element which is engaged to said first element.

10. The high pressure seal recited in claim 9, wherein said first element includes a threaded portion and said hand tightenable connector is threadable thereto.

11. The high pressure seal recited in claim 9 wherein said ferrule is fixed to said second element and said hand tightenable connector is moveable proximally thereof along said second element.

12. The high pressure seal recited in claim 11 wherein said ferrule includes a force bearing surface and said hand tightenable connector is moveable against said force bearing surface.

13. The high pressure seal recited in claim 12 wherein said hand tightenable connector is kept captive by said ferrule.

14. The high pressure seal recited in claim 9 wherein said hand tightenable connector and said ferrule are constructed and arranged for mateable engagement.

15. The high pressure seal recited in claim 14 wherein said ferrule includes a projection which is receivable within a chamber in said hand tightenable connector.

16. The high pressure seal recited in claim 15 wherein said ferrule includes an annular sidewall and a central projection and said hand tightenable connector includes a chamber for receiving said central projection.

17. The high pressure seal recited in claim 1 further including a fluid jet cutting system that supplies pressurized fluid to an instrument that creates a fluid jet, the system including:
   a pump for providing a fluid at a pressure, said pump having an inlet communicatable with a source of a fluid, and an outlet through which the pumped fluid passes; and,
   a delivery tube fluidly connecting said outlet of said pump to the instrument that creates a fluid jet;
   Wherein said first element is the outlet of said pump and said second element is said delivery tube.

18. The high pressure seal recited in claim 1 further including a fluid jet cutting system that supplies pressurized fluid to an instrument that creates a fluid jet, the system including:
   a pump for providing a fluid at a pressure, said pump having an inlet communicatable with a source of a fluid, and an outlet through which the pumped fluid passes; and,
   a delivery tube fluidly connecting said outlet of said pump to said instrument that creates a fluid jet;
   wherein said first element is said instrument for creating a fluid jet and said second element is said delivery tube.

19. The high pressure seal recited in claim 1 wherein said second element is a high pressure delivery tube.

20. The high pressure seal recited in claim 19, wherein said high pressure seal allows a pressurized fluid to be communicated through said high pressure delivery tube to said lumen of said first element at pressures greater than 1,000 psi, in a leaktight fashion.

21. The high pressure seal recited in claim 1 wherein said first and second elements are releasably engaged to each other so as to provide a quick disconnect of said first and second elements.

22. The high pressure seal recited in claim 21 wherein said deformable seal is carried by said second element as said first and second elements are disconnected.

* * * * *